(12) United States Patent
Müller et al.

(10) Patent No.: US 6,284,514 B1
(45) Date of Patent: Sep. 4, 2001

(54) BACTERIAL STRAIN CORYNEBACTERIUM. SP K2-17 AND METHOD FOR THE MICROBIAL DECONTAMINATION OF MATERIALS WHICH ARE CONTAMINATED WITH COMPOUNDS FROM PHENOXYALCANOIC ACID-HERBICIDE PRODUCTION

(75) Inventors: Roland Müller; Wolfgang Babel, both of Leipzig (DE)

(73) Assignee: UFZ-Umweltforschungszentrum Leipzig-Halle GmbH (DE)

( * ) Notice: Subject to any disclaimer, the term of this patent is extended or adjusted under 35 U.S.C. 154(b) by 0 days.

(21) Appl. No.: 09/331,223

(22) PCT Filed: Dec. 20, 1997

(86) PCT No.: PCT/EP97/07162

§ 371 Date: Aug. 23, 1999

§ 102(e) Date: Aug. 23, 1999

(87) PCT Pub. No.: WO98/28043

PCT Pub. Date: Jul. 2, 1998

(30) Foreign Application Priority Data

Dec. 20, 1996 (DE) ............................... 196 54 624

(51) Int. Cl.$^7$ ............................... B09B 3/00; C02F 3/00; C12N 1/00; C12N 1/20; D06M 16/00
(52) U.S. Cl. ................ 435/252.1; 210/600; 210/601; 435/262.5; 435/264; 435/821; 435/822
(58) Field of Search ............................... 435/252.1, 262.5, 435/264, 821, 822; 210/600, 601

(56) References Cited

FOREIGN PATENT DOCUMENTS

4424756 * 1/1996 (DE) .

OTHER PUBLICATIONS

Dietmar Pieper et al.; Metabolism of 2,4–dichlorophenoxyacetic Acid, 4–chloro–2–methylphenoxyacetic acid and 2–methylphonexyacetic Acid by *Alcalignees eutrophus* JMP 134; Arch Microbiol (1988) 150; pp. 95–102.*
Manfred Horvath, et al.; Isolation and Characterization of a 2–(2,4–dichlorophenoxy) propionic acid–degrading soil bacterium; Applied Microbiology Biotechnology (1990) 33; p. 213–216.*
Sisko Kilpi; Degradation of Some Phenoxy Acid Herbicides by Mixed Cultures of Bacteria Isolated from Soil Treated with 2–(2–Methyl–4–Chloro)Phenoxypropionic Acid; Microbial Ecology 6 (1980) pp. 261–270.*

Kevin Short et al.; Survival and degradative capacity of *Pseudomonas putida* induced or constitutively expressing plasmid–mediated degration of 2, 4–dichlorophenoxyacetate (TFD) in soil; Can.J. Microbiol.36 (1990) pp. 821–826
J.Tiedje et al.; 2,4–D Metabolism: Pathway of Degradation of Chlorocatechols by *Arthrobacter* sp.; J. Agr. Food Chem. vol. 17, No. 5 Sep.–Oct. 1969; pp. 1021–1026.
R. Haugland et al; Degradation of the Chlorinated Phenoxyacetate Herbicides 2,4–Dichlorophenoxyacetic Acid and 2,4,5–Trichlorophenoxyacetic Acid by Pure and Mixed Bacterial Cultures; Applied and Environmental Microbiology, May 1990; pp. 1357–1362.
H.Lappin et al; Degradation of the Herbicide Mecoprop [2–Methyl–4–Chlorphenoxy) Propionic Acid] by a Synergistic Microbial Community; Applied and Environmental Microbiology, Feb. 1985; pp. 429–433.
K.Oh et al; Degradation of 2,4–dichlorophenoxyacetic acid by mixed cultures of bacteria; Journal of Industrial Microbiology, 6 (1990) pp. 275–278.
U. Lechner et al.; Degradation of 4–chloro–2–methylphenol by an activated sludge isolage and its taxonomic description; Biodegradation 6 (1995) pp. 83–92.
D. Hoffmann et al.; Isolation and Characterization of an Alkaliphilic Bacterium Capable of Growing on 2,4–Dichlorophenoxyacetic Acid and 4–Chloro–2–methylphenoxyacetic Acid; Acta Biotechnol. 16 (1996) 2–3; pp. 121–131.
O.Maltseva et al.; Degradation of 2,4–dichlorophenoxyacetic acid by haloalkaliphilic bacteria; Microbiology (1996) 142, pp. 1115–1122.
R. Müller et al.; Degradation of Phenoxyalkanoic Acid Herbicides by a Facultatively Alkaliphilic Bacterium, *Comamonas acidovorans* P4a; Ist. International Symp. Extrimophiles, Estoril, Portugal Jun. 1996 p. 208.
Bloedorn, I.; Ph.D. Thesis 1990, Halle University.
K. Horikoshi: "Microorganisms in Alkaline Environments", VCH Weinheim, New York, 1991 (book).

* cited by examiner

Primary Examiner—Deborah K. Ware
(74) Attorney, Agent, or Firm—Norris, McLaughlin & Marcus P.A.

(57) ABSTRACT

The invention relates to the new bacterial strain Corynebacterium sp. K2-17 and to a process for the microbial decontamination of materials polluted with compounds from the production of phenoxyalkanoic acid herbicides, such as 2,4-dichlorophenoxybutyric acid (DCPB), 4-chloro-2-methylphenoxybutyric acid (MCPB), 2,4-dichlorophenoxyacetic acid (2,4-D), 4-chloro-2-methylphenoxyacetic acid (MCPA), 2,4-dichlorophenol (DCP), and 4-chloro-2-methylphenol (MCP) in a pH range of from slightly acidic to strongly alkaline.

13 Claims, No Drawings

BACTERIAL STRAIN CORYNEBACTERIUM. SP K2-17 AND METHOD FOR THE MICROBIAL DECONTAMINATION OF MATERIALS WHICH ARE CONTAMINATED WITH COMPOUNDS FROM PHENOXYALCANOIC ACID-HERBICIDE PRODUCTION

The invention relates to the new bacterial strain Aureobacterium sp. K2-17 and to a process for the microbial decontamination of materials polluted with compounds from the production of phenoxyalkanoic acid herbicides, such as 2,4-dichlorophenoxybutyric acid (DCPB), 4-chloro-2-methylphenoxybutyric acid (MCPB), 2,4-dichlorophenoxyacetic acid (2,4-D), 4-chloro-2-methylphenoxyacetic acid (MCPA), 2,4-dichlorophenol (DCP), and 4-chloro-2-methylphenol (MCP) in a pH range of from slightly acidic to strongly alkaline.

The chemical industry production sites where herbicides have been manufactured for decades, as well as the vicinities thereof are contaminated with starting materials, intermediates, and final products of said production. This involves soils, surface waters and ground waters in these areas but also the production plants and buildings themselves. Inter alia, this also implies former production sites of phenoxyalkanoic acid herbicide manufacturing. The compounds present for this reason, such as DCPB, MCPB, 2,4-D, MCPA, DCP, and MCP are known to be toxic, and some of them have cancerogenic and teratogenic effects. The dismantling of chemical plants where these compounds have been manufactured, and the crushing of masonry in shredding plants gives rise to rubble which has to be decontaminated in order to remove these harmful compounds, thereby avoiding health hazards of exposed persons and also protecting flora and fauna.

In addition to contaminated rubble, there are also aqueous waste flows highly polluted with these substances. As a result, the contaminations also reach the soils and ground waters in the vicinity of such (former) sites. The disposal of waters from the production of such compounds therefore requires special concern because they contain these harmful components in a concentrated form. Namely, it has been found that introducing these production waters into industrial clarification plants may give rise to significant interference of the biological equilibrium and thus, the performance of these plants, affecting the rate and degree of degradation. An effective solution of the contamination problem requires special conditions and implies various preconditions.

Various processes on a physical-chemical basis are known for the decontamination of solid matrices such as rubble. Thus, while thermal processes are effective, their disadvantage lies in their high cost. In addition, extraction or washing processes with subsequent absorptive removal of pollutants—even in the event of polluted waters—for decontaminating solid matrices are well-known. However, they merely transfer the problem to another carrier, although sometimes in a highly concentrated form, and consequently give rise to the above-mentioned drawbacks as well.

Owing to the vast metabolic potential of microorganisms, decontamination processes on a microbial basis are preferred. Thus, microbial methods generally are effective and low-cost variants wherein organic compounds undergo degradation to produce biomass, water, carbon dioxide, and heat. To this end, indigenous microorganisms adapted to the corresponding medium can be employed. By optimizing the conditions, the metabolic potential can be utilized to full extent As a result of growth, the biocatalytic potential is even increased in a quasi autocatalytic fashion. However, it is also possible to add ex situ cultivated microorganisms (species or consortia) as starting cultures to contaminated materials where redevelopment may be conducted in most various processing regimes (i.e., in situ, on site, off site, reactors, pits, and the like). With polluted and concentrated waters, separate treatment and degradation in reactors could be performed.

The actual sites, i.e., the waters and ground waters, as well as soils, may also be subjected to microbial treatment, be it for plants during running production or those sites which, following discontinuation of production and dismantling of plants, are to be recultivated or put to new utilization. It is disadvantageous that the pH values of these sites range from slightly acidic to alkaline. Aqueous eluates from concrete demolition are even strongly alkaline, correspondingly restricting the variety of the microorganism species and posing special preconditions on decontamination on a microbial basis.

The productive decontamination of chlorinated and methylated phenols and phenoxyalkanoic acids in the neutral pH range using single cultures (Pieper, D. H. et al., Arch. Microbiol. 150 (1988) 95; Horvath, M. et al., Appl. Microbiol. Biotechnol. 33 (1990) 213; Kilpi, S., Microbiol. Ecol. 6 (1980) 261; Short, K. A. et al., Can. J. Microbiol. 36 (1990) 822; Tiedje, J. M. et al., J. Agr. Food Chem. 17 (1969) 1021) and consortia (Bloedorn, I., Ph.D. Thesis 1990, Halle University; Haugland, R. A. et al., Appl. Env. Microbiol. 56 (1990) 1357; Lappin, H. M., Appl. Env. Microbiol. 49 (1985) 429; Oh, K. H. and Tuovinen, O. H., J. Ind. Microbiol. 6 (1990) 275) is well-known. The degradation of 2,4-dichlorophenol and 4-chloro-2-methylphenol by a Gram-negative bacterium, strain S1, has been described by Lechner et al. (Biodegradation 6, 1995, 83).

As has been set forth, there is an additional complication in that these contaminations occur in strongly alkaline media. This is the medium of the so-called alkaliphiles (K. Horikoshi: "Microorganisms in Alkaline Environments", VCH Weinheim, New York, 1991). Recently, it has been demonstrated that microorganisms concentrated from such contaminated masonry are capable as consortia of completely degrading various phenoxyalkanoic acid derivatives in aqueous eluates having pH values of up to 12.5 (Müller et al., DE 44 24 756.7).

Likewise, corresponding alkaliphilic pure cultures are known which are capable of degrading phenoxyacetic acid derivatives (Hoffmann et al., Acta Biotechnol. 16 (1996) 121; Maltseva et al., Microbiology 142 (1996) 1115; Müller et al., 1st Internat. Symp. Extremophiles, Estoril, 1996, Portugal, p. 208). Compared to consortia, however, monocultures are restricted in their metabolic spectrum. Indeed, they have the advantage of easier handling, but contaminations from herbicide production frequently contain a spectrum of phenoxyalkanoic acid derivatives. To date, no microorganisms are known that would be capable of degrading phenoxybutyric acid herbicides such as DCPB/MCPB in an alkaline medium as well.

SUMMARY OF THE INVENTION

Therefore, it was the basic object of the invention to develop a practicable and cost-effective process for the microbial decontamination of material polluted with compounds from the phenoxyalkanoic acid herbicide production, find and combine strains of microorganisms suitable for complete degradation of said compounds. In particular, these microorganisms should be usable in the microbial decontamination of, inter alia, eluates from demolition materials of buildings and plants, or from waste waters and ground waters.

A new bacterial strain has been found which is excellently suited for use in the degradation of DCPB and/or MCPB in a range of from slightly acidic to alkaline. It is the strain Aureobacterium sp. K2-17. It has been deposited with the Deutsche Sammlung von Mikroorganismen und Zellkulturen GmbH under the number DSMZ 11288 on Nov. 18, 1996.

Said strain grows in a range of from neutral to alkaline and, surprisingly, is capable of cleaving DCPB and MCPB to form the corresponding phenol derivatives and $C_4$ derivatives.

DESCRIPTION OF THE PREFERRED EMBODIMENT

Aureobacterium sp. K2-17 is cultivated according to per se usual methods in a continuous or discontinuous fashion, or by using other strategies of feeding, e.g., either on a complex medium containing yeast extract and/or peptone, where a pH value of from 7 to 9.5 may be pre-adjusted, or using n-alkanoic acids (acetate, butyrate), dicarboxylic acids (succinate), or other suitable carbon/energy sources. Following addition of the phenoxybutyric acids, these compounds are degraded without a substantial delay.

In a preferred embodiment of the invention, said new strain, Aureobacterium sp. K2-17, is combined with a DCP/MCP-mineralizing strain, thereby achieving complete degradation of the pollutants.

It is particularly preferred to employ the strain C. acidovorans P4a (DSMZ 10474) as DCP/MCP-utilizing strain.

C. acidovorans P4a is also cultivated according to per se usual methods and preferably, it is grown on 2,4-D or MCPA with addition of up to 0.25 parts by weight of yeast extract per part by weight of herbicide, or from 1 to 10 parts by weight of Na acetate or another short-chain alkanoic acid per part by weight of herbicide, preferably at a pH of from 7 to 9.

Surprisingly, the combination of said new strain, Aureobacterium sp. K2-17, and the C. acidovorans P4a strain allows complete degradation both in a slightly acidic to neutral pH range and in a strongly alkaline medium, thereby decontaminating the affected masonry or the corresponding aqueous medium.

The degradation of herbicides via growth and propagation is conducted under aerobic conditions and preferably, a temperature range of from 10 up to 38EC is selected. The pH value preferably ranges from 6–12.5.

Another embodiment comprises combinations of Aureobacterium sp. K2-17 with other well-known DCP/MCP-degrading strains such as the strain S1 described by Lechner et al. in Biodegradation 6 (1995) 83, whereby degradation in a pH range of from slightly acidic to neutral can also be accomplished.

In addition, one major advantage of combining the Aureobacterium sp. K2-17 strain with C. acidovorans P4a is that C. acidovorans P4a is suitable for use in degrading 2,4-D and/or MCPA, so that a broad spectrum of compounds from the phenoxyalkanoic acid herbicide production will be completely degraded.

Cultivation of the strains is carried out either separately or in admixture. In a preferred embodiment, direct cultivation on materials containing DCPB and/or MCPB, possibly 2,4-D and/or MCPA, and possibly DCP and/or MCP is performed, so that these compounds will be completely degraded in the presence of per se usual growth components.

The decontamination process according to the invention using Aureobacterium sp. K2-17 may be conducted continuously by offering aqueous media polluted with DCPB and/or MCPB as a source of carbon and energy. As has been set forth, another DCP/MCP-degrading strain is a precondition for complete degradation, where the per se usual growth components such as nitrogen and phosphorus must be present at appropriate concentrations.

Using Aureobacterium sp. K2-17 as DCPB- and/or MCPB-cleaving strain and C. acidovorans P4a as DCP/MCP utilizer, similar steady-state biomass concentrations are obtained for both species of bacteria over a pH range of from 6 to 10 under these conditions. At pH values of up to 8.5 the growth rates, i.e., the substrate conversion rates range around 0.05 h$^{-1}$ or 2.5 mmol/gBTSAh and drop to 10–20% of these values at pH values around 10. Theses herbicides undergo quantitative degradation, with formation of bacterial biomass, water, $CO_2$, HCl, and heat.

The decontamination may also be conducted in a partially discontinuous fashion by adding to a system an appropriately produced biomass as inoculum suited to catalyze the decontamination of a herbicide-polluted material in an aqueous phase.

The process may also be operated in a fixed-bed reactor using, e.g., a pit technique, or in a liquid-phase reactor. The process may be operated in a continuous, partially continuous (e.g. fed-batch), or discontinuous fashion. Depending on the selected processing regimen, measures for retaining the biomass could be advantageous.

The biomass is added at a concentration of preferably from 0.1 to 1 g/kg to a material contaminated with DCPB/MCPB and possibly with 2,4-D and/or MCPA at a total concentration of up to 2 g/kg in an aqueous medium which may have pH values of about 6 through up to 12.5.

Under these conditions, the decontamination with respect to DCPB/MCPB cleavage with intermediate formation of DCP/MCP and their complete mineralization proceeds at a rate of up to 2.5 mmol/gBTSAh if both species are used as an admixture of equal parts by weight. The rate can be nearly doubled by mixing Aureobacterium sp. K2-17 and C. acidovorans P4a at a ratio of 2:1. Such conversion rates apply for pH values of about 6 to 8.5. Increasing the pH value up to 10 will not substantially change the ratio of the two species, but the rate will drop to values of 10–20%.

In particular, the process of the invention is advantageously employed in the treatment of building rubble, e.g. at chemical industry sites, or in areas or storage and shipment centers contaminated with these substances, or in the treatment of waters from the production of these compounds, or in the treatment of soils, surface waters and ground waters contaminated with these herbicides.

It has been found that the results of the invention are also obtained when using instead of Aureobacterium sp. K2-17 a DCPB/MCPB-cleaving bacterial strain which exhibits activity in a pH range of 8–10 and is viable up to pH values of 12. For example, such strains are Rhodococcus erythropolis K2-12, Bacillus sp. K2-8, or Clavibacter michiganenesis K2-16.

Instead of Aureobacterium sp. K2-17 however, it is also possible to employ a DCPB/MCPB-cleaving bacterial strain which exhibits activity in a slightly acidic or neutral pH range.

Without intending to limiting, the invention will now be illustrated with reference to the following embodiments.

EXAMPLE 1

The Aureobacterium sp. K2-17 and Comamonas acidovorans P4a strains are applied on a minimal medium. Per gram of biomass to be formed, this medium has the following composition (in mg/l): $NH_4Cl$: 700; $KH2PO_4$: 158; $MgSO_4H7H_2O$: 8; $CaCl_2H2H_2O$: 10; $FeSO_4H7H_2O$: 2.5; $ZnSO_4H7H_2O$: 0.23; $MnSO_4H4H_2O$: 0.42; $CuSO_4H5H_2O$: 0.39; $Na_2MoO_4$: 0.12.

Cultivation is effected in a pH range of from 6 to 10 at 30EC and a dissolved oxygen concentration of >30% of the air saturation value. Yeast extract and peptone at concentrations of 10 g/l each are used as source of carbon and energy for the growth of Aureobacterium sp. K2-17. *C. acidovorans* P4a is cultivated on 2,4-D and/or MCPA or salts thereof. Na acetate at a weight ratio of 1:1–10 is offered as an additional carbon/energy source. Immediate feeding of a minimal medium containing the components MCPB/DCPB and 2,4-D/MCPA or/and DCP/MCP as source of carbon and energy is also possible, where both strains grow simultaneously. The growth rates are adjusted to 0.05–0.1 $h^{-1}$. Once stable growth conditions are reached, this culture can be used to decontaminate waters polluted with phenoxybutyric and/or phenoxyacetic acid derivatives. The aqueous media polluted with these herbicides are fed at rates of up to 0.1 $h^{-1}$. When having stable process operation, the pH value is to be maintained within a range of from 6 to 10, preferably 8 to 9. If the decontamination is effected in a productive fashion, nitrogen and phosphorus, for example, must be present in appropriate amounts. Feeding of trace elements can be neglected when using natural waters. Under these preconditions, complete degradation of DCPB/MCPB, as well as 2,4-D/MCPA and DCP/MCP is possible at these rates. The degradation can be monitored using spectrophotometric or chromatographic (HPLC) methods, or via the release of, e.g. chloride, or via the change of the AOX value.

EXAMPLE 2

Both cultures are produced as mixtures or grown in separate batches. They are applied on carrier matrices in a suitable fashion, through which a flow of water is passed containing the respective phenoxyalkanoic acids. On the one hand, the flow rate must be adapted to the biocatalytic potential, so that complete degradation occurs following passage. On the other hand, the process can be operated in a cycle to complete mineralization, using recirculation. The process can be designed as a biopit process, where it is merely necessary to take care for appropriate moistening and ventilation and, if the concentrations of the phenoxyalkanoic acid are high compared to the inoculum concentration, feeding of macro-elements is advantageous.

What is claimed is:

1. A biologically pure Aureobacterium sp. strain DSMZ 11288.

2. A process for the microbial decontamination of materials polluted with compounds from the production of phenoxyalkanoic acid herbicides, comprising the step of contacting the polluted materials with the biologically pure Aureobacterium sp. strain DSMZ 11288 in a range of from slightly acidic to alkaline at pH values between 6 and 12.5 under aerobic conditions at temperatures between 10 and 38° C.

3. The process according to claim 2, wherein the biologically pure Aureobacterium sp. strain DSMZ 11288 is cultivated continuously or discontinuously during said process.

4. The process according to claim 3, wherein the biologically pure Aureobacterium sp. strain DSMZ 11288 is directly cultivated on the polluted materials.

5. The process according to claim 2, wherein the decontamination of said polluted materials is conducted continuously, partially continuously or discontinuously during said process.

6. The process according to claim 2, wherein the decontamination is performed in a fixed-bed reactor or a liquid-phase reactor.

7. The process according to claim 2, wherein the phenoxyalkanoic acid herbicides are selected from the group consisting of 2,4-dichlorophenoxybutyric acid (DCPB); 4-chloro-2-methylphenoxybutyric acid (MCPB); 2,4-dichlorophenoxyacetic acid (2,4-D); 4-chloro-2-methylphenoxyacetic acid (MCPA); 2,4-dichlorophenol (DCP); and 4-chloro-2-methylphenol (MCP).

8. The process according to claim 7, wherein the biologically pure Aureobacterium sp. strain DSMZ 11288 is used in combination with a DCP/MCP-mineralizing bacterial strain in said step of contacting the polluted materials.

9. The process according to claim 8, wherein said DCP/MCP-mineralizing bacterial strain is *Comamonas acidovorans* P4a strain DSMZ 10474.

10. The process according to claim 9, wherein the strains Aureobacterium sp. strain DSMZ 11288 and the *Comamonas acidovorans* P4a strain are employed at pH values of from 6 to 8.5 at a ratio of 2:1.

11. The process according to claim 7, wherein one or both of DCPB and MCPB are present in the polluted materials, and are degraded by contact with the biologically pure Aureobacterium sp. strain DSMZ 11288.

12. The process according to claim 9, wherein the biologically pure Aureobacterium sp. strain DSMZ 11288 and the *Comamonas acidovorans* P4a strain are cultivated continuously or discontinously during said process.

13. The process according to claim 12, wherein the bacteria strains are directly cultivated on the polluted materials.

* * * * *